United States Patent
Drew et al.

(10) Patent No.: US 12,419,754 B2
(45) Date of Patent: Sep. 23, 2025

(54) JOINT IMPLANTS HAVING POROUS STRUCTURES FORMED UTILIZING ADDITIVE MANUFACTURING AND RELATED SYSTEMS AND METHODS

(71) Applicant: Encore Medical, LP, Austin, TX (US)

(72) Inventors: Alex Drew, Austin, TX (US); Jeremy Borchert, Cedar Park, TX (US); John Green, Leander, TX (US); Rachel Patel, Austin, TX (US)

(73) Assignee: Encore Medical, LP, Austin, TX (US)

( * ) Notice: Subject to any disclaimer, the term of this patent is extended or adjusted under 35 U.S.C. 154(b) by 0 days.

(21) Appl. No.: 18/673,174

(22) Filed: May 23, 2024

(65) Prior Publication Data

US 2024/0390153 A1 Nov. 28, 2024

Related U.S. Application Data

(60) Continuation of application No. 18/108,521, filed on Feb. 10, 2023, now Pat. No. 12,016,780, which is a division of application No. 16/986,051, filed on Aug. 5, 2020, now Pat. No. 11,589,996, which is a continuation of application No. PCT/US2020/024710, filed on Mar. 25, 2020.

(51) Int. Cl.
| | |
|---|---|
| *A61F 2/38* | (2006.01) |
| *A61F 2/30* | (2006.01) |
| *B22F 10/85* | (2021.01) |
| *B33Y 50/00* | (2015.01) |
| *G06F 30/17* | (2020.01) |

(52) U.S. Cl.
CPC ........ *A61F 2/3877* (2013.01); *A61F 2/30942* (2013.01); *B22F 10/85* (2021.01); *B33Y 50/00* (2014.12); *G06F 30/17* (2020.01); *A61F 2002/30011* (2013.01); *A61F 2002/30113* (2013.01); *A61F 2002/30952* (2013.01); *A61F 2002/3096* (2013.01); *A61F 2002/30968* (2013.01); *A61F 2002/3097* (2013.01); *A61F 2002/30985* (2013.01); *A61F 2310/00023* (2013.01)

(58) Field of Classification Search
CPC ................ A61F 2/3877; A61F 2/30942; A61F 2002/30011; A61F 2002/30113; A61F 2002/30952; A61F 2002/3096; A61F 2002/30968; A61F 2002/3097; A61F 2002/30985; A61F 2310/00023; B22F 10/85; B33Y 50/00; G06F 30/17
USPC ................................. 623/20.18, 20
See application file for complete search history.

(56) References Cited

U.S. PATENT DOCUMENTS

| | | | | |
|---|---|---|---|---|
| 12,016,780 B2 * | 6/2024 | Drew | .................. | A61F 2/30771 |
| 2018/0333780 A1 * | 11/2018 | Klein | ...................... | B22F 10/38 |

* cited by examiner

*Primary Examiner* — Michael J Brown
(74) *Attorney, Agent, or Firm* — Eversheds Sutherland (US) LLP

(57) ABSTRACT

A medical implant which comprises a porous lattice is fabricated with additive manufacturing techniques such as direct metal laser sintering. A CAD model of the porous lattice is created by defining a trimming volume and merging some lattice elements with adjacent solid substrate.

20 Claims, 8 Drawing Sheets

JOINT IMPLANTS HAVING POROUS STRUCTURES FORMED UTILIZING ADDITIVE MANUFACTURING AND RELATED SYSTEMS AND METHODS

RELATED APPLICATIONS

This application is a continuation of U.S. patent application Ser. No. 18/108,521, filed on Feb. 10, 2023, which application is a divisional of U.S. patent application Ser. No. 16/986,051, filed on Aug. 5, 2020, which application is a continuation of, and claims priority to, International Patent Application No. PCT/US20/24710, filed on Mar. 25, 2020. The contents of the aforementioned priority applications are hereby incorporated by reference in their entireties.

BACKGROUND

The present disclosure relates generally to biomedical implants, and more specifically to methods and apparatuses directed to additive manufacturing of porous structures for such biomedical implants.

Traditionally, the manufacture of biomedical implants has incorporated the application of spray-on or roughened porous materials or layers to pre-formed biomedical implants to facilitate attachment and ingrowth of tissues to the implants. More recently, the manufacture of biomedical implants have alternatively or additionally utilized additive manufacturing techniques, also referred to as 3-dimensional printing, to generate porous structures for biomedical implants.

Embodiments described herein improve upon existing additive manufacturing techniques for generating porous structures.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

A method for fabricating an implant device comprising a porous lattice is provided. The method includes creating, by a computing device, a model of the implant device comprising the porous lattice. The creating includes defining an initial lattice volume having a bounding surface for the implant device. The creating includes populating the initial lattice volume with a plurality of seed points. The creating includes populating the initial lattice volume with a plurality of nodes and struts that divide the initial lattice volume into a plurality of 3-dimensional regions, thereby defining an initial lattice. The creating includes defining a second volume within the initial lattice volume such that a trimming boundary is defined between the initial lattice volume and the second volume. The creating includes removing struts and nodes, and portions thereof from the model that are located outside the trimming boundary. The creating includes fabricating the implant device comprising the porous lattice at least in part by exposing fusible material to a heating source according to the model.

Another method for fabricating an implant device comprising a porous lattice is provided. The method includes creating, by a computing device, a model of the implant device comprising the porous lattice. The creating includes defining an initial lattice volume having a bounding surface for the implant device. The creating includes populating the initial lattice volume with a plurality of seed points. The creating includes populating the initial lattice volume with a plurality of nodes and struts that connect the nodes to divide the initial lattice volume into a plurality of 3-dimensional regions, thereby defining an initial lattice. The creating includes attracting one or more nodes and/or struts toward a substrate of the implant device such that at least one attracted node or strut is positioned coincident with or at least partly within the substrate of the implant device. The creating includes merging some or all of the attracted nodes and/or struts with the substrate of the implant device.

Yet another method for fabricating an implant device comprising a porous lattice is provided. The method includes creating, by a computing device, a model of the implant device comprising the porous lattice. The creating includes defining an initial lattice volume having a bounding surface for the implant device. The creating includes populating the initial lattice volume with a plurality of seed points. The creating includes populating the initial lattice volume with a plurality of nodes and struts that divide the initial lattice volume into a plurality of 3-dimensional regions, thereby defining an initial lattice. The creating includes defining a second volume within the initial lattice volume such that a trimming boundary is defined between the initial lattice volume and the second volume. The creating includes removing struts and nodes, and portions thereof from the model that are located outside the trimming boundary.

An implant device made by any method(s) described herein are also provided.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

Figure 1:
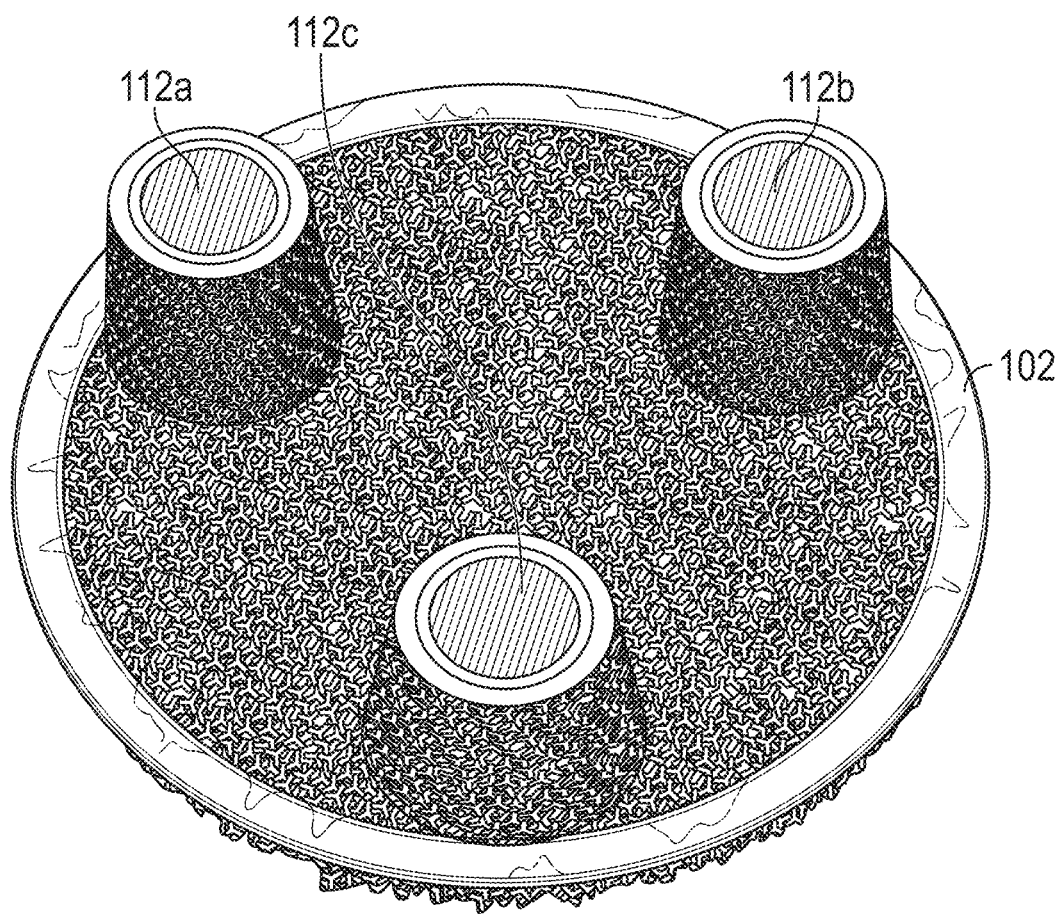
FIG. 1 illustrates a bone-facing side of a patellar implant, as fabricated with additive manufacturing, according to some embodiments.

The following description and examples e some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to implants for use in joint arthroplasty and more specifically to methods and apparatuses directed to additive manufacturing of implants, for example patellar implants, utilizing direct metal laser sintering (DMLS), for use in cementless total knee arthroplasty.

General Interpretive Principles for the Present Disclosure

Various aspects of the novel systems, apparatuses, and methods are described more fully herein with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Discussion of Several Exemplary Embodiments of the Present Disclosure

Initial discussion of an example implant fabricated in accordance with this disclosure will be described in connection with FIGS. 1-2B. Example techniques for fabricating such implants will then be described in more detail in connection with FIGS. 3-12. The specific example described in detail herein is a patellar implant, but the design and fabrication methods and systems described herein could be applied to any implant where a porous structure is desirable.

FIG. 1 illustrates a bone-facing side 110 of a patellar implant 102, including a porous lattice 114, as fabricated with additive manufacturing, according to some embodiments. In some embodiments, patellar implant 102 can comprise a solid titanium alloy substrate, for example Ti-6Al-4V. However, the present application is not so limited and patellar implant 102 can additionally or alternatively comprise any suitable metal, alloy, polymer or other material. Bone-facing side 110 of patellar implant 102 can comprise one or more posts 112a, 112b, 112c (112a-112c) configured to anchor bone, for example the patella, of the patient to patellar implant 102. During a healing process subsequent to implantation, the patient's bone may adhere to bone-facing side 110 of patellar implant 102, including to posts 112a-112c, thereby anchoring patellar implant 102 in place. Porous lattice 114 can comprise generally linearly extending struts that meet at nodes. Node and strut position may be a randomized or pseudo-randomized structure, for example based on a 3-dimensional Voronoi tessellation and may be fabricated in a single step utilizing additive manufacturing techniques, as will be described in more detail below. While not illustrated in FIG. 1, patellar implant 102 also comprises a joint-facing, or articulating, side opposite bone-facing side 110 that is substantially contoured appropriately for abutting the knee joint of a patient.

Figure 2A:
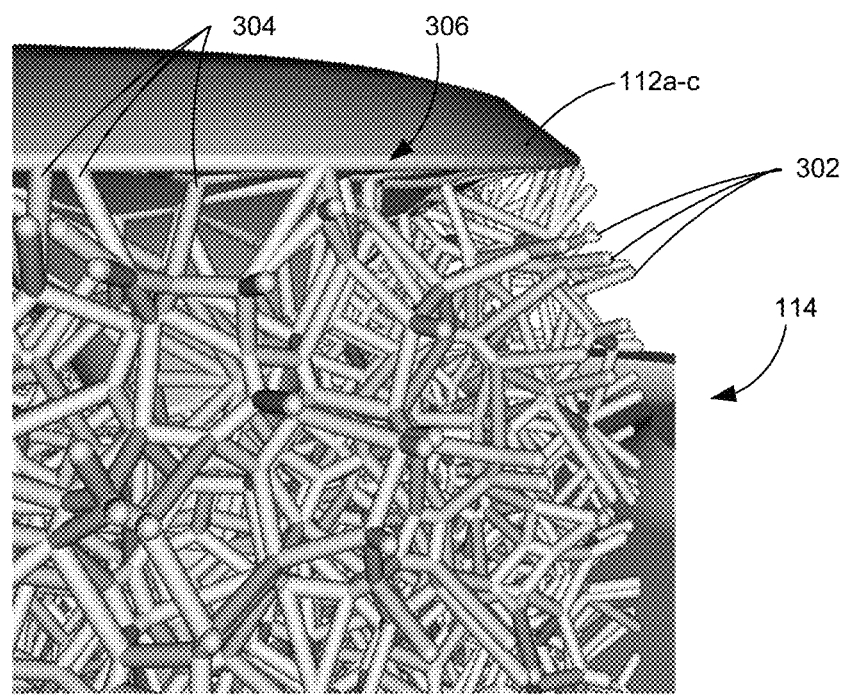
FIG. 2A illustrates a CAD model of a porous lattice comprising struts integrated with a periphery of an implant, according to some embodiments.

FIG. 2A illustrates a magnified CAD model of porous lattice 114 as integrated with patellar implant 102, according to some embodiments. As previously described, porous lattice 114 can comprise a randomized or pseudo-randomized structure based on a 3-dimensional Voronoi tessellation, which can produce a Gaussian distribution of pore diameters centered around a desired mean pore diameter while maintaining a desired level of overall porosity to facilitate bone in-growth and implant securement during the healing process. Porous lattice 114 may comprise a plurality of open ended (e.g., cantilevered from a node), struts 302 at its exterior, bone-facing surface to increase surface roughness and initial bone in-growth and fixation. Porous lattice 114 may further comprise a plurality of struts 304 that integrate with edge features 306 of the solid substrate of patellar implant 102 to ensure sufficient mechanical support and to provide a robust connection between porous lattice 114 and the solid substrate of patellar implant 102. FIG. 2B illustrates a magnified view of porous lattice 114, as actually fabricated, according to some embodiments.

Figure 2B:
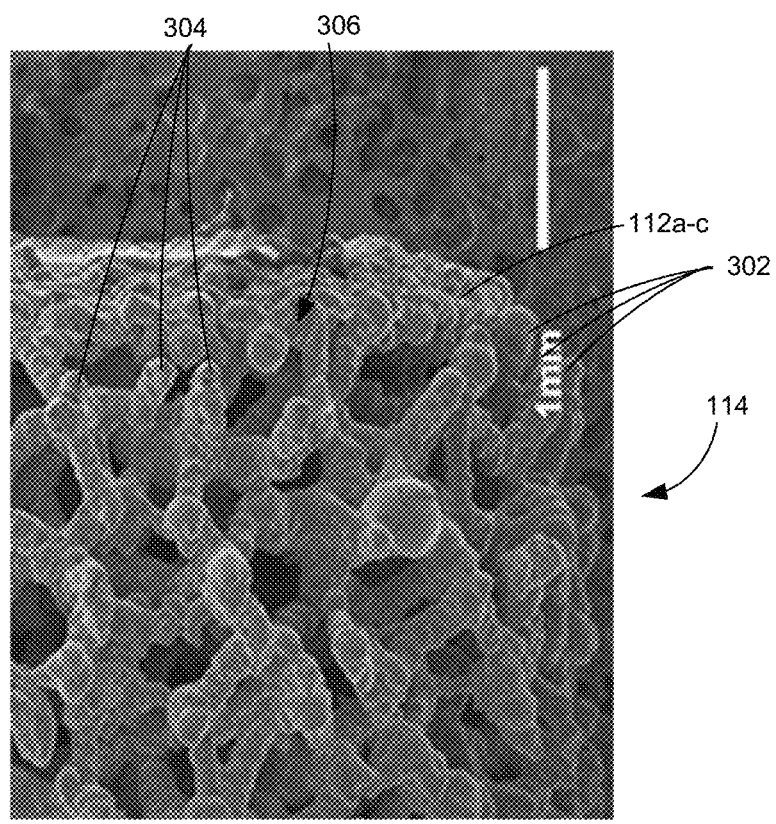
FIG. 2B illustrates the porous lattice of FIG. 2A, as fabricated with additive manufacturing, according to some embodiments.

Although FIGS. 2A and 2B illustrate the plurality of struts 304 integrating with edge features 306 of patellar implant 102 at posts 112a-c, the present disclosure is not so limited and the plurality of struts 304 can also integrate with edge features of patellar implant 102 along substantially all surfaces of patellar implant that abut porous lattice 114, for example at least a portion of bone-facing surface 110 of patellar implant 102 and/or at least portions of top surfaces of posts 112a-c (see, e.g., FIG. 1).

An example process for generating a CAD model of porous lattice 114 integrated with patellar implant 102 and their subsequent fabrication will now be described in more detail in connection with FIGS. 3-12.

Figure 3:
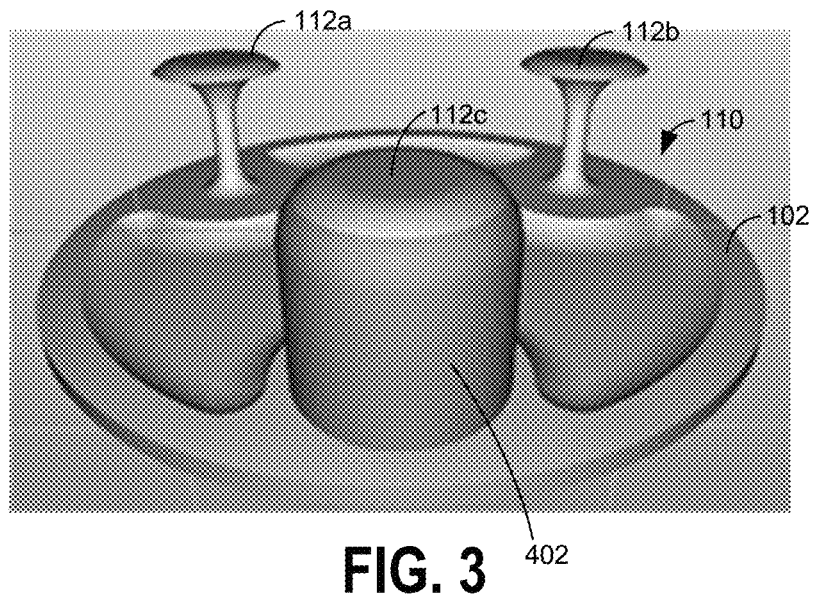
FIG. 3 illustrates a CAD model of an initial volume for containing a porous lattice of an implant substrate, according to some embodiments.

FIG. 3 illustrates a CAD model of an initial volume 402 intended to contain porous lattice 114 of patellar implant 102, according to some embodiments. Initial volume 402 and the solid substrate of patellar implant 102 can be designed using standard CAD techniques including lattice-modeling computer software, for example Element by nTopology of New York, NY and/or Autodesk Within Medical by Autodesk of San Rafael, CA. Although initial volume 402 is illustrated as having a substantially cylindrical shape and an outer boundary that curves to substantially match the slope of patellar implant 102 at the abutting edge features of post 112c, the present disclosure is not so limited and initial volume 402 may have any suitable shape defined by any suitable outer boundary.

Initial volume 402 can be populated with a plurality of seed points. The 3-dimensional distribution of at least some of these seed points can be random or pseudo-random and can be performed repeatably on identical volumes, for example similar volumes surrounding the remaining posts 112a, 112b. In some embodiments, the distribution of these seed points can be based on a Poisson-disc sampling strategy, for example as described by Gamito MN, Maddock SC, Accurate Multi-dimensional Poisson-disc Sampling, ACM Transactions on Graphics (2009) 29, 1, Article 8 (December 2009), which is hereby incorporated by reference in its entirety. Using Poisson-disc sampling allows for specification of seed points that will result in a desired target cell size when a Voronoi tessellation is subsequently applied to sub-divide initial lattice volume 402.

Figure 4:
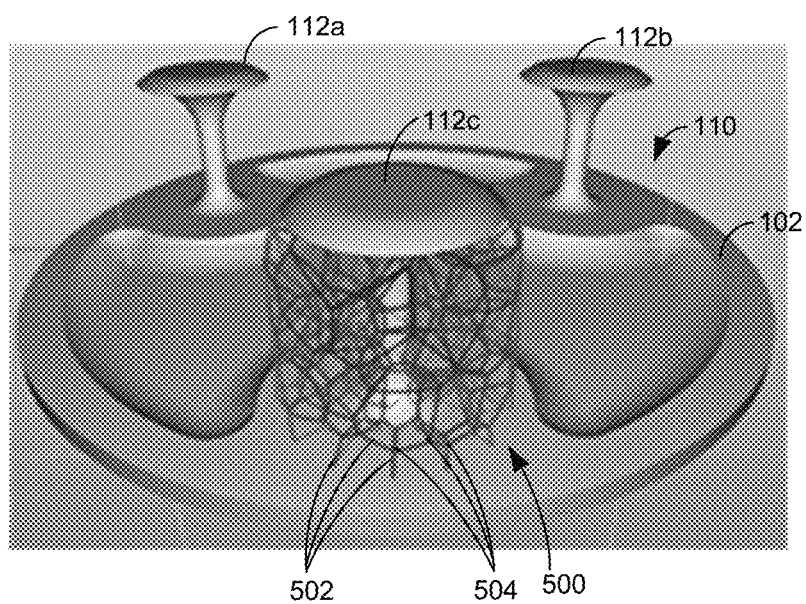
FIG. 4 illustrates a CAD model of the volume of FIG. 3 containing a plurality of nodes and struts forming the porous lattice, according to some embodiments.

FIG. 4 illustrates a CAD model of initial volume 402 subdivided into a plurality of 3-dimensional regions by a plurality of struts 502. As noted above, in some implementations, positions of struts and nodes may be defined according to a Voronoi tessellation. As shown in FIG. 4, a Voronoi tessellation may be utilized to define a plurality of nodes connected by a plurality of struts 502, subdividing initial volume 402 into a plurality of 3-dimensional regions.

The generalized n-dimensional Voronoi tessellation technique was defined by Voronoi, Georges in the early 20$^{th}$ century. (See for example, "Nouvelles applications des parametres continus a la theorie des forms quadratiques." Premier Memoire. Sur quelques proprietes des forms quadratiques positives parfaits . . . " Journal fur die reine und angewandte Mathematik 133 (1908): 97-178; Voronoi, Georges, and "Nouvelles applications des parametres continus a la theorie des forms quadratiques. Deuxieme Memoire. Recherches sur les parallelloedres primitifs . . . " Journal fur die reine und angewandte Mathematik 134 (1908): 198-287; 136 (1909): 67-181 . . . . Example algorithmic implementations of Voronoi tessellation are described in Guibas, et al., "Randomized incremental construction of Delaunay and Voronoi diagrams," Algorithmica (1992) 7:381-413, which is hereby incorporated by reference in its entirety.

The resulting lattice 500 comprises a plurality of struts 502 that extend along the mating boundaries of adjacent subdivided 3-dimensional regions of initial volume 402, and a plurality of nodes 504 which define positions where struts 502 intersect with one another. Strut and node locations may be defined by the locations of the plurality of seed points used by the Voronoi tessellation.

The distribution of seed points may be made to have some non-random or non-pseudo-random characteristics. For example, the sampling strategy employed to generate seed point location (such as various strategies described in Gamito, as previously described) can be biased to have a higher point density in some regions of the lattice than others. This could be done to improve lattice characteristics by, for example, generating an increasing density of seed points from the outer boundary of the lattice to the inner boundary of the lattice. This can increase lattice mechanical strength without significantly degrading bone in-growth properties of the lattice. Of course, even within a random distribution of points, different regions can be defined that have varying point density, and as noted above, there still can be considerable randomness in the point positioning in local regions. In this case, a different point density in one region than another means a point density difference not reasonably producible by a random or pseudo-random process alone.

Figure 5:
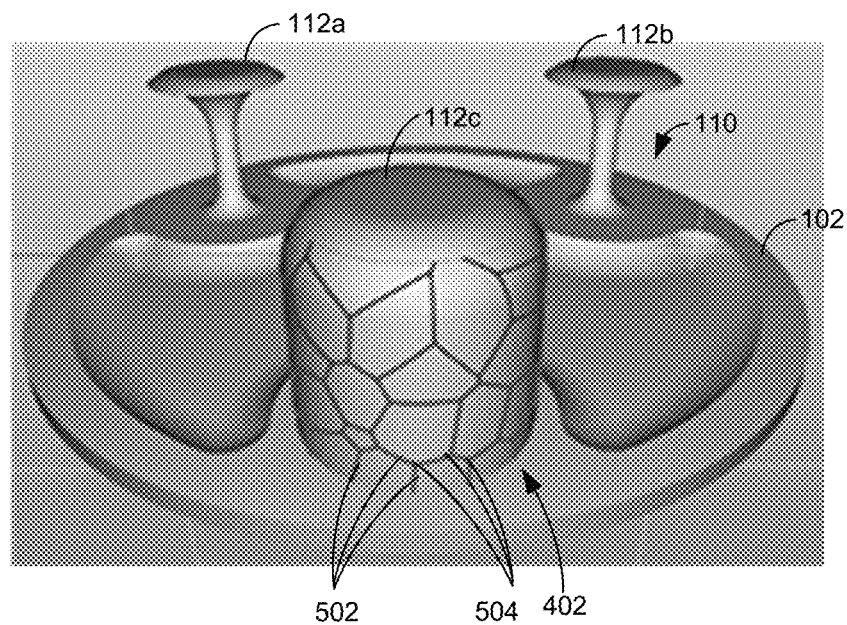
FIG. 5 illustrates a CAD model comprising a plurality of struts extending along an outer boundary of the initial volume of FIG. 4, according to some embodiments.

FIG. 5 illustrates a CAD model showing the plurality of struts 502 that extend along an outer boundary of initial volume 402, according to some embodiments. To increase the surface roughness of lattice 500, a trimming volume may be defined that is partly or wholly on the interior of initial volume 402. At least some struts 502 that conform to the bone-facing outer boundary of initial volume 402 are outside the trimming volume, and at least some struts extend through the surface of the trimming volume out to the surface of the initial volume 402. Portions of lattice 500 within the trimming volume may be kept in the model, while portions of lattice 500 within initial volume 402 but not within the trimming volume may be removed from the model. Accordingly, an outer layer between the outer surface of the initial volume 402 and the outer surface of the trimming volume may be trimmed away by removing from the model struts and nodes outside the trimming volume. Struts of the model that intersect the surface of the trimming volume may be terminated at or near the point of intersection, producing an outer surface of open-ended struts with free strut ends as mentioned above.

Figure 6:
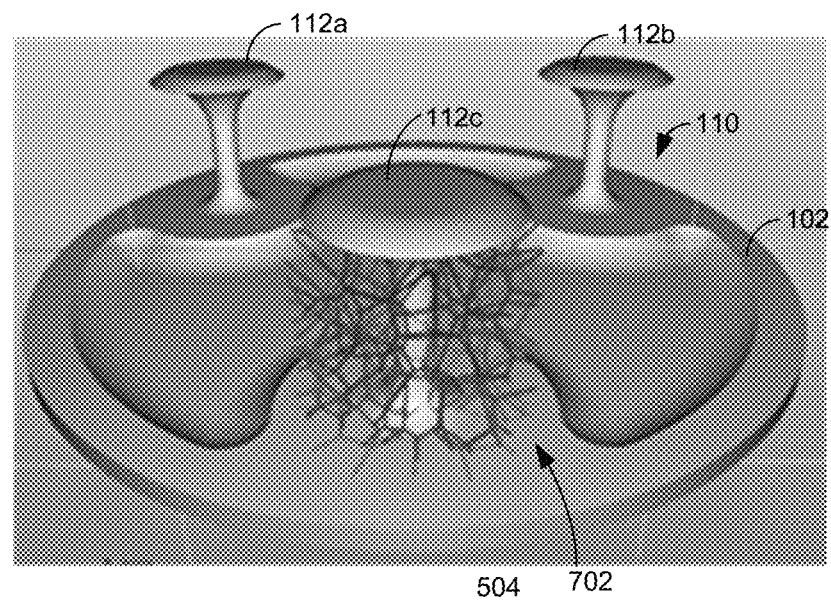
FIG. 6 illustrates a CAD model of the initial volume of FIG. 5 trimmed to exclude at least some of the plurality of nodes and struts extending along the outer boundary of the initial volume, according to some embodiments.

An example of the result of such lattice trimming is shown in FIG. 6, which illustrates a CAD model of a trimmed lattice 702 where the model has been modified by eliminating at least portions of the plurality of struts 502 outside the trimming boundary. In some implementations, the free struts may be manipulated after trimming by having their initial end position and/or orientation with respect to the trimming volume boundary. This can improve manufacturability of the lattice or modify physical properties of the lattice such as strength or coefficient of friction. For example, a group of free strut ends may be extended further outward from the trimming volume boundary than the remaining free strut ends. The group may be selected as a randomly or pseudo-randomly selected subset of free strut ends that numbers some percentage of the total number of free strut ends. The angle of orientation of the struts with free ends with respect to the trimming volume boundary can also be manipulated. For example, the angle from the surface normal can be contained within a particular range. Any struts with free strut ends outside this angle could be rotated toward the normal vector at the boundary intersection point to be at an angle from the normal that is somewhere within the normal range. This re-orientation could be randomized or pseudo-randomized. For example, for each strut that is outside the desired angular range and thus requires re-orientation, a random or pseudo-random angle within the desired range could be selected, and each strut could be re-oriented to be at the angle from normal selected for that strut. It will be appreciated that both of the above described free strut manipulations could be performed on the same trimmed lattice structure such that some or all free strut ends are changed in both length and orientation.

Figure 7:
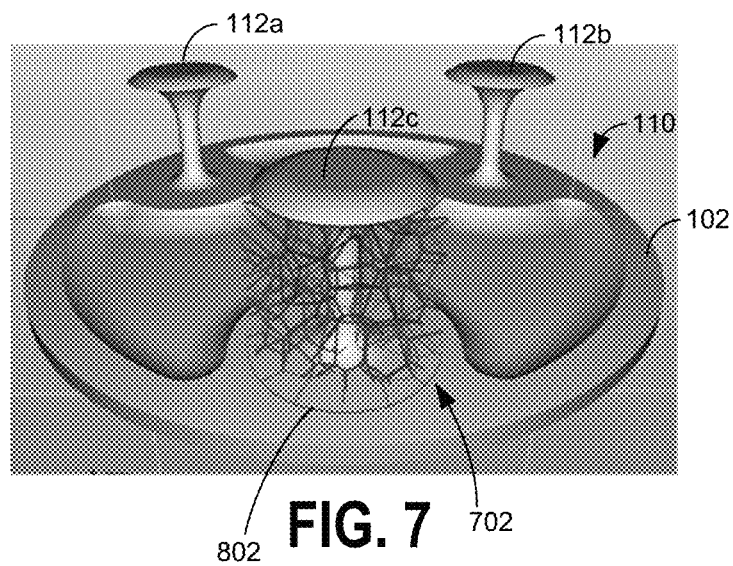
FIG. 7 illustrates a CAD model of a trimmed porous lattice, according to some embodiments.
Figure 8:
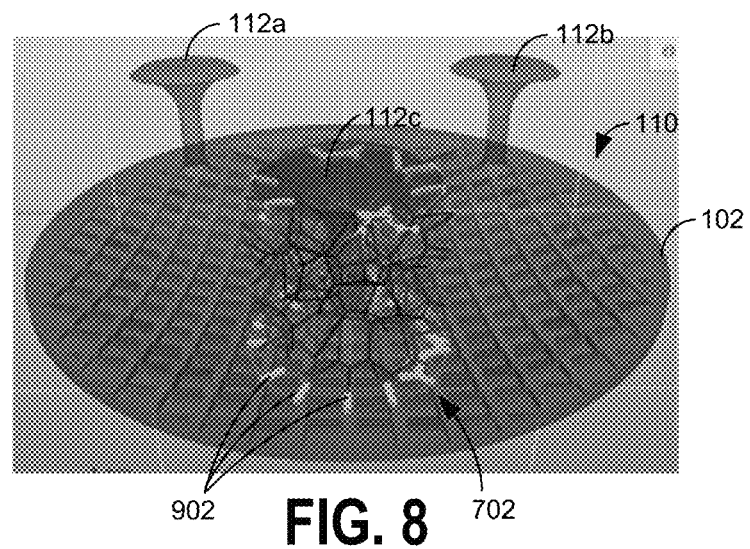
FIG. 8 illustrates a CAD model of the trimmed lattice of FIG. 7 having one or more struts and/or nodes proximate to the implant substrate, attracted to the implant substrate, according to some embodiments.
Figure 9:
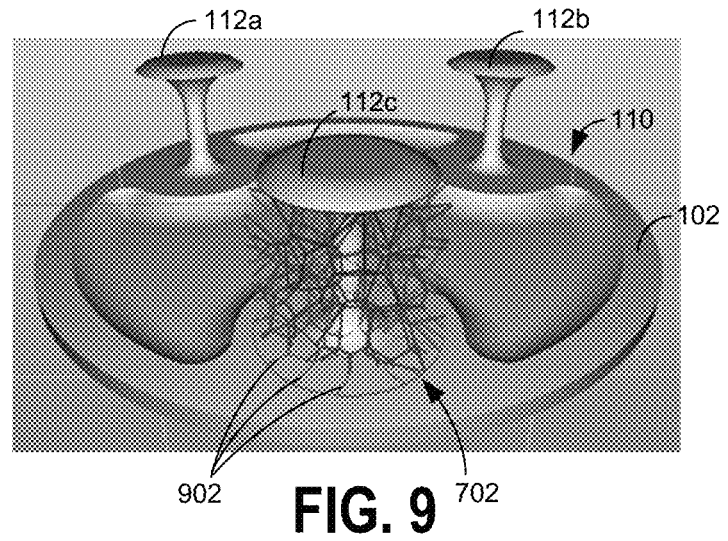
FIG. 9 illustrates a CAD model of the trimmed volume of FIG. 8 having the one or more attracted struts and nodes merged with the implant substrate, according to some embodiments.

To further improve integration of trimmed lattice 702 with the solid substrate of patellar implant 102, at least some of the nodes of trimmed lattice 702 immediately adjacent to the solid substrate of patellar implant 102, and the associated struts, are attracted to the solid substrate of patellar implant 102 such that the attracted nodes and at least portions of the associated struts are positioned within the model boundary of the solid substrate of patellar implant 102. For example, FIG. 7 illustrates a CAD model of trimmed lattice 702 substantially similar to FIG. 6, however, further visually indicating a boundary 802 of trimmed lattice volume 702 on the solid substrate of patellar implant 102. FIG. 8 illustrates a CAD model of trimmed lattice 702 having one or more nodes and associated struts 902, immediately adjacent to the solid substrate of patellar implant 102, attracted to the solid substrate of patellar implant 102. FIG. 8 further illustrates bone-facing side 110 of patellar implant 102 as translucent for ease of visualization of the attraction step. FIG. 9 illustrates a CAD model of trimmed lattice 702 having the one or more attracted nodes and associated struts 902 merged with the solid substrate of patellar implant 102.

Once the attracted nodes and struts of trimmed lattice 702 have been merged with the solid substrate of patellar implant 102, all or a portion of struts 502 can be thickened to a suitable and/or desired thickness and/or cross-sectional geometry, for example a substantially circular cross-sectional geometry. However, any suitable cross-sectional geometry for struts 502 is also contemplated. In some implementations, strut characteristics can be made to vary for different regions of the lattice. One use for such a procedure can be to obtain similar benefits to the biased seed point distribution described above. In this implementation, the cross-sectional diameter of a particular strut can be made to vary as a linear, non-linear, stepped, or any other function of the shortest distance between a given point on the strut (e.g. the center point or an end point) and a point on the outer boundary. This distance may define a scale factor that is multiplied by a minimum cross-sectional area to define the cross-sectional area of that particular strut. If the function increases with increasing distance from the outer boundary, the struts will gradually thicken from the outer boundary to the inner boundary of the lattice, producing a decreasing porosity from the outer surface inward.

By utilizing the above-described process, an implant, for example patellar implant 102, having a large volume porous lattice model for an implant can be created with a single step of strut and node definition. Prior tessellation methods have required additional computation for aligning and joining individually tessellated sub-volumes of a larger overall desired volume for the porous lattice. Thus, such above-described processes may eliminate steps of joining multiple tiles or multiple subdivided volumes of separately generated lattices or of resolving redundant features therein, providing a more efficient design and/or fabrication process. In addition, the process of trimming the outer surface of the volume after creating a larger volume of lattice is an efficient way of generating open-ended struts that extend outward from the overall surface of the lattice at a variety of angles, including struts that extend normal or near normal to the overall surface of the lattice.

The above-described CAD modeling and fabrication process(es) can be performed utilizing a computing device 1100, as described in connection with FIG. 10 below, and/or a fabricating device 1200, as described in connection with FIG. 11 below. While computing device 1100 and fabricating device 1200 are illustrated and described as separate devices, the present disclosure is not so limited and computing device 1100 and fabricating device 1200 may be disposed within the same device.

Figure 10:
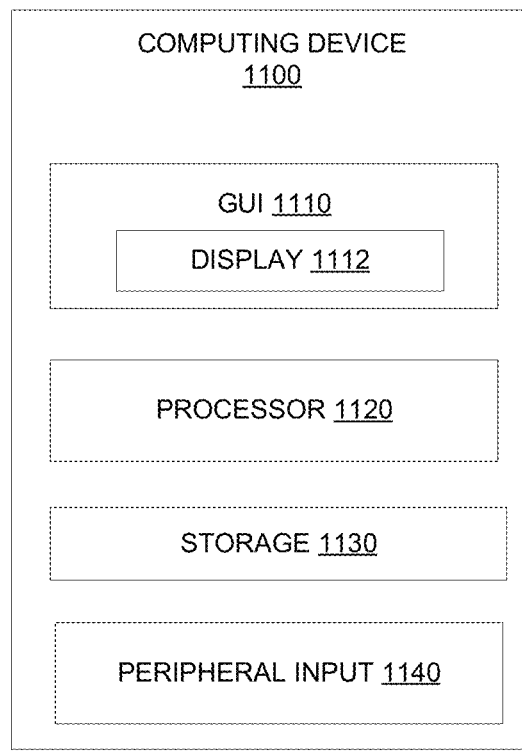
FIG. 10 illustrates a computing device configured to generate a CAD model of an implant comprising a conformal, porous lattice, according to some embodiments.

FIG. 10 illustrates a computing device 1100 configured to generate a CAD model of an implant comprising a porous lattice, according to some embodiments. Computing device 1100 can comprise storage 1130, which can comprise computer memory configured to store one or more CAD programs, for example Element by nTopology of New York, NY and/or Autodesk Within Medical by Autodesk of San Rafael, CA. Storage 1130 may also be configured to store a CAD model of an implant as previously described in connection with any of FIGS. 1-9.

Computing device 1100 can further comprise a processor 1120 configured to perform one or more operations to thereby generate a CAD model of an implant as previously described, based on non-transitory, computer-readable instructions held within storage 1130.

Computing device 1100 can further comprise a graphical user interface (GUI) 1110, which can include a display 1112 configured to display the CAD model to a designer and/or user. Computing device 1100 can further comprise an input/output 1140 configured to accept user input and output CAD files for the models created with the principles set forth above. In some embodiments, input/output 1140 may be incorporated within GUI 1110, although the present disclosure is not so limited.

Figure 11:
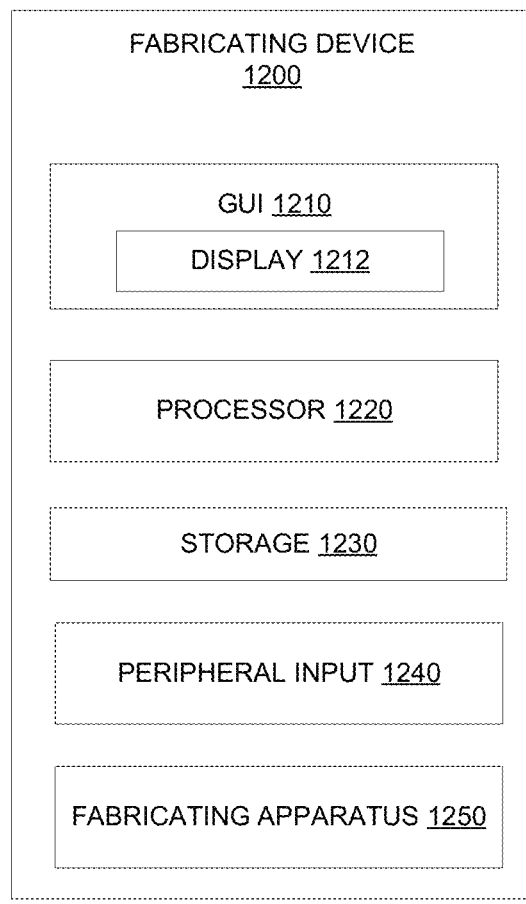
FIG. 11 illustrates an additive manufacturing device configured to fabricate an implant device comprising a porous lattice based on at least one CAD model, according to some embodiments.

FIG. 11 illustrates a fabricating device 1200 configured to fabricate an implant device comprising a porous lattice based on at least one CAD model, according to some embodiments. In some embodiments, fabricating device 1200 can utilize additive manufacturing (AM) techniques, such as direct metal laser sintering (DMLS), which selectively exposes layers of fusible material, e.g., titanium or a titanium alloy, to a heating source, e.g., a laser. Such techniques are well known, for example as described by Abe, et al., "Manufacturing of Titanium Parts for Medical Purposes by Selective Laser Melting," Proceedings of The Eighth International Conference on Rapid Prototyping (Jun. 12-13, 2000) 288-293, which is hereby incorporated by reference in its entirety.

In addition and/or alternative to any or all features described in Abe, et al., fabricating device 1200 can include storage 1230, which can comprise computer memory configured to store one or more CAD models for use in fabricating an implant device comprising a porous lattice as well as one or more computer programs configured to control the laser and other operations of the fabricating device to fabricate the implant device comprising the porous lattice, based on the one or more CAD models as previously described in connection with any of FIGS. 1-9.

Fabricating device 1200 can further comprise a processor 1220 configured to perform one or more operations for fabricating the implant based on the one or more CAD models as previously described, based on non-transitory, computer-readable instructions held within storage 1230.

Fabricating device 1200 can further comprise a graphical user interface (GUI) 1210, which can include a display 1212 configured to display information related to the fabrication process to a user. Fabricating device 1200 can further comprise a peripheral input device 1240 configured to accept user input. In some embodiments, peripheral input device 1240 may be incorporated within GUI 1210, although the present disclosure is not so limited.

Fabricating device 1200 can further include a fabricating apparatus 1250, which may comprise any and all equipment for performing the DMLS AM techniques, at least as described by Abe, et al.

Figure 12:
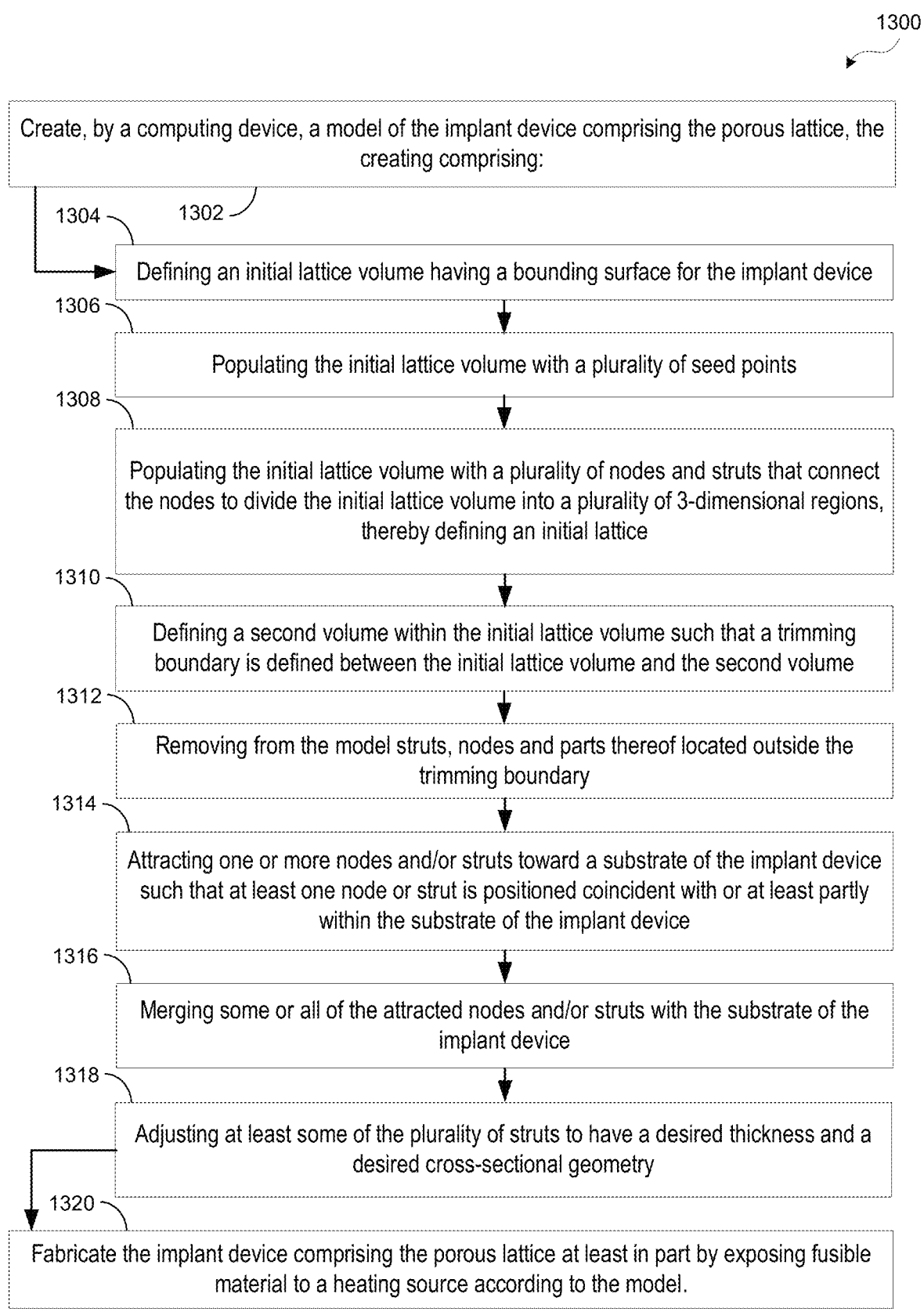
FIG. 12 illustrates a flowchart of a method for fabricating an implant device comprising a conformal, porous lattice, according to some embodiments.

FIG. 12 illustrates a flowchart 1300 of a method for fabricating an implant device comprising a porous lattice, according to some embodiments. Flowchart 1300 may be performed in whole or in part by either or both of computing device 1100 and fabricating device 1200 of FIGS. 10 and 11, as previously described in connection with any of FIGS. 1-11.

At block 1302, flowchart 1300 includes creating, by a computing device, a model of the implant device comprising the porous lattice. For example, computing device 1100 of FIG. 10 may be configured to create a CAD model of patellar implant 102 comprising porous lattice 114. Porous lattice 114 may comprise a Gaussian distribution of pore diameters of a desired width at half-maximum that is centered around a desired mean pore diameter. Patellar implant 102 comprises at least one post 112a-112c configured to anchor bone of a patient to patellar implant 102. As previously described, the creating process of block 1302 may comprise one or more steps, blocks and/or processes as described by one or more of blocks 1304 to 1320 below.

At block 1304, flowchart 1300 includes defining an initial lattice volume having a bounding surface for the implant device. For example, processor 1120 of computing device 1100 may be configured to define initial lattice volume 402 having a bounding surface for patellar implant 102.

At block 1306, flowchart 1300 includes populating the initial lattice volume with a plurality of seed points. For example, processor 1120 of computing device 1100 may be configured to populate initial lattice volume 402 with a plurality of seed points. A distribution of the seed points can be pseudo-random, for example based on a Poisson-disc sampling strategy as previously described.

At block 1308, flowchart 1300 includes populating the initial lattice volume with a plurality of nodes and struts that connect the nodes to divide the initial lattice volume into a plurality of 3-dimensional regions, thereby defining an initial lattice. Each 3-dimensional region encloses a respective seed point of the plurality of seed points. For example, processor 1120 of computing device 1100 may be configured to populate initial lattice volume 402 and with a plurality of nodes 504 and struts 502 that connect the nodes to divide initial lattice volume 402 into a plurality of 3-dimensional regions and thereby define initial lattice 500. As illustrated, each strut 502 can connect two nodes 504. This block may be carried out utilizing Voronoi tessellation as previously described.

At block 1310, flowchart 1300 includes defining a second volume within the initial lattice volume such that a trimming boundary is defined between the initial lattice volume and the second volume. For example, processor 1120 of computing device 1100 may be configured to define a second volume within initial lattice volume 402 such that a trimming boundary is defined between initial lattice volume 402 and the second volume.

At block 1312, flowchart 1300 includes removing from the model struts and nodes located outside the trimming boundary. For example, processor 1120 of computing device 1100 may be configured to removed struts and nodes located within initial lattice volume 402 but not within the second volume. This node and strut removal converts initial lattice 500 to trimmed lattice 702, which excludes at least portions of struts 502 outside the trimming boundary.

At block 1314, flowchart 1300 includes attracting one or more nodes and/or struts toward a substrate of the implant device such that at least one node or strut is positioned coincident with or at least partly within the substrate of the implant device. For example, processor 1120 of computing device 1100 may be configured to attract one or more nodes and/or struts toward a substrate of patellar implant 102 such that at least one node or strut is positioned coincident with or at least partly within the substrate of patellar implant 102.

At block 1316, flowchart 1300 includes merging some or all of the attracted nodes and/or struts with the substrate of the implant device. For example, processor 1120 of computing device 1100 may be configured to merge some or all of the attracted nodes 504 and/or struts 502 with the substrate of patellar implant 102.

At block 1318, flowchart 1300 includes adjusting at least some of the plurality of struts to have a desired thickness and a desired cross-sectional geometry. For example, processor 1120 of computing device 1100 may be configured to thicken at least some of struts 502 to have a desired thickness and/or a desired cross-sectional geometry, e.g., a substantially circular geometry.

At block 1320, flowchart 1300 includes fabricating the implant device comprising the porous lattice at least in part by exposing fusible material to a heating source according to the model. For example, processor 1220 may be configured to direct fabricating apparatus 1250 of fabricating device 1200 (FIG. 11) to fabricate patellar implant 102 comprising porous lattice 114 at least in part by exposing fusible material, e.g., titanium or a titanium alloy, to a heating source, e.g., a laser, according to the CAD model.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A method for fabricating an implant device comprising a porous lattice, the method comprising:
   creating, by a computing device, a model of the implant device comprising the porous lattice, the creating comprising:
      defining an initial lattice volume having a bounding surface for the implant device;
      populating the initial lattice volume with a plurality of seed points,
      populating the initial lattice volume with a plurality of nodes and struts using a Voronoi tessellation to divide the initial lattice volume into a plurality of 3-dimensional regions, thereby defining an initial lattice;
      defining a second volume within the initial lattice volume such that a trimming boundary is defined between the initial lattice volume and the second volume;
      removing struts and nodes, and portions thereof from the model that are located outside the trimming boundary; and
   fabricating the implant device comprising the porous lattice at least in part by exposing fusible material to a heating source according to the model.

2. The method of claim 1, wherein a distribution of the plurality of seed points is at least partially random or pseudo-random.

3. The method of claim 1, wherein the distribution of seed points has a higher density in some regions of the lattice than others.

4. The method of claim 1, wherein a distribution of the plurality of seed points is based at least in part on a Poisson-disc sampling strategy.

5. The method of claim 1, wherein all locations within each 3-dimensional region are closer to the respective seed point than to any other seed point.

6. The method of claim 1, wherein creating the model of the implant device further comprises adjusting at least some of the plurality of struts to have a desired thickness and a desired cross-sectional geometry.

7. The method of claim 6, wherein the adjusting varies in different regions of the lattice.

8. The method of claim 7, wherein the adjusting is different at different distances from an outer surface of the lattice.

9. The method of claim 6, wherein the desired cross-sectional geometry is a substantially circular geometry.

10. The method of claim 1, wherein the porous lattice comprises a Gaussian distribution of pore diameters centered around a desired mean pore diameter in at least one region of the lattice.

11. The method of claim 1, wherein the implant device comprises at least one post configured to anchor bone of a patient to the implant device.

12. The method of claim 1, wherein the implant device comprises a patellar implant.

13. The method of claim 1, wherein the fusible material comprises titanium or a titanium alloy.

14. The method of claim 1, wherein the heating source comprises a laser.

15. A method for generating a fabrication model for an implant device comprising a porous lattice, the method comprising:
   creating, by a computing device, a model of the implant device comprising the porous lattice, the creating comprising:
      defining an initial lattice volume having a bounding surface for the implant device;
      populating the initial lattice volume with a plurality of seed points;
      populating the initial lattice volume with a plurality of nodes and struts using a Voronoi tessellation to divide the initial lattice volume into a plurality of 3-dimensional regions, thereby defining an initial lattice;
      defining a second volume within the initial lattice volume such that a trimming boundary is defined between the initial lattice volume and the second volume; and
      removing struts and nodes, and portions thereof from the model that are located outside the trimming boundary.

16. The method of claim 15, wherein a distribution of the plurality of seed points is at least partially random or pseudo-random.

17. The method of claim 15, wherein the distribution of seed points has a higher density in some regions of the lattice than others.

18. The method of claim 15, wherein a distribution of the plurality of seed points is based at least in part on a Poisson-disc sampling strategy.

19. The method of claim 15, wherein all locations within each 3-dimensional region are closer to the respective seed point than to any other seed point.

20. The method of claim 15, wherein creating the model of the implant device further comprises adjusting at least some of the plurality of struts to have a desired thickness and a desired cross-sectional geometry.

* * * * *